(12) United States Patent
Baek et al.

(10) Patent No.: US 10,085,652 B2
(45) Date of Patent: Oct. 2, 2018

(54) OPTICAL MEASURING DEVICE FOR CARDIOVASCULAR DIAGNOSTICS

(71) Applicant: QUALCOMM Incorporated, San Diego, CA (US)

(72) Inventors: David Boettcher Baek, San Diego, CA (US); Russell Gruhlke, Milpitas, CA (US); Evgeni Poliakov, San Mateo, CA (US); Khurshid Alam, Mountain View, CA (US); Lars Lading, Roskilde (DK)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 15/074,482

(22) Filed: Mar. 18, 2016

(65) Prior Publication Data

US 2017/0265753 A1    Sep. 21, 2017

(51) Int. Cl.
| | | |
|---|---|---|
| *A61B 5/021* | (2006.01) | |
| *A61B 5/02* | (2006.01) | |
| *A61B 5/00* | (2006.01) | |
| *A61B 5/024* | (2006.01) | |

(52) U.S. Cl.
CPC .......... *A61B 5/021* (2013.01); *A61B 5/02416* (2013.01); *A61B 5/02438* (2013.01); *A61B 5/6801* (2013.01); *A61B 5/6826* (2013.01); *A61B 2562/0233* (2013.01)

(58) Field of Classification Search
CPC ..... A61B 5/0062; A61B 5/0082; A61B 5/021; A61B 5/02416; A61B 5/02438; A61B 5/681

USPC .................................... 600/476, 479, 480
See application file for complete search history.

(56) References Cited

U.S. PATENT DOCUMENTS

| | | | |
|---|---|---|---|
| 6,031,603 A | 2/2000 | Fine et al. | |
| 6,475,153 B1 | 11/2002 | Khair et al. | |
| 7,674,231 B2 | 3/2010 | McCombie et al. | |
| 8,672,854 B2 | 3/2014 | McCombie et al. | |

(Continued)

OTHER PUBLICATIONS

Fei P., et al.,"Cardiac Light-Sheet Fluorescent Microscopy for Multi-Scale and Rapid Imaging of Architecture and Function", Scientific Reports, Mar. 3, 2016, vol. 6 (1), pp. 1-12, XP055368468, DOI:10.1038/srep22489.

(Continued)

*Primary Examiner* — Allen Porter, Jr.
(74) *Attorney, Agent, or Firm* — Kilpatrick Townsend & Stockton

(57) ABSTRACT

An optical sensor and a method of using the optical sensor in an optical measuring device that measures cardiovascular properties and compensates for movement artifacts by directing a sheet of light towards an artery. The optical sensor may include one or more light sources, one or more transmit light guides coupled to the one or more light sources and configured to direct light from the one or more light sources as a sheet of light towards an artery, such that the cross-sectional profile of the sheet of light may have a length transverse to a longitudinal direction of the artery that is longer than the diameter of the artery. The optical sensor may include one or more light detectors configured to receive backscattered light and generate an output based on the received backscattered light that is a reflection of the sheet of light from the artery and surrounding tissues.

32 Claims, 12 Drawing Sheets

(56) References Cited

U.S. PATENT DOCUMENTS

| | | |
|---|---|---|
| 2004/0036424 A1* | 2/2004 | Hsieh ................ H05B 33/0803 315/291 |
| 2004/0236227 A1 | 11/2004 | Gueissaz |
| 2010/0160794 A1 | 6/2010 | Banet et al. |
| 2014/0070957 A1 | 3/2014 | Longinotti-Buitoni et al. |
| 2015/0164352 A1 | 6/2015 | Yoon et al. |
| 2015/0223708 A1 | 8/2015 | Richards et al. |

OTHER PUBLICATIONS

International Search Report and Written Opinion—PCT/US2017/019160—ISA/EPO—May 26, 2017.

* cited by examiner

OPTICAL MEASURING DEVICE FOR CARDIOVASCULAR DIAGNOSTICS

BACKGROUND

Devices for measuring cardiovascular properties suffer from the problem that the measurement itself interferes strongly with the state of the subject, thereby leading to erroneous results. For example, current cuff-based methods for obtaining blood pressure measurements may impart a significant physiological impact. In current cuff-based methods, blood pressure measurements are obtained by constricting an artery to the extent that blood flow is completely blocked and then slowly releasing the constriction. Constricting the artery affects pulse pressure propagation and pulse pressure shapes. Further, the diastolic pressure is derived from measurements obtained when the transmural pressure (i.e., pressure difference between the outside and the inside of an artery) is close to zero, which implies those measurements are made under conditions that are far from normal.

In addition, traditional methods based on inflatable cuffs and measurements performed in a clinical environment may have strong psychological effects causing changes in a patient's blood pressure. For example, the psychological effects of being in a clinical environment may cause an elevation in the patient's blood pressure. The phenomenon is commonly called "white coat syndrome" or "white coat hypertension." In an additional example, a patient's blood pressure may be elevated during normal daily activities but not in a clinical environment. This phenomenon is commonly called "masked hypertension."

Additionally, blood pressure often exhibits considerable variability over time. Thus, identifying diurnal or other temporal variations in blood pressure may be important for proper diagnosis of various cardiovascular issues, including hypertension. It has also been shown that performing ambulatory blood pressure measurements may be beneficial for improved diagnosis by facilitating measurements over longer time periods and avoiding the psychological effects typical in clinical environments.

SUMMARY

Various embodiments include an optical sensor and a method of using the optical sensor in an optical measuring device that measures cardiovascular properties and compensates for movement artifacts by directing a sheet of light towards an artery of interest. In various embodiments, the optical sensor may include one or more light sources, one or more transmit light guides coupled to the one or more light sources and configured to direct light from the one or more light sources as a sheet of light towards an artery in a subject, such that the cross-sectional profile of the sheet of light may have a length transverse to a longitudinal direction of the artery that is longer than the diameter of the artery. The optical sensor may also include one or more light detectors configured to receive backscattered light that is light from the sheet of light that is backscattered by the artery and tissues surrounding the artery.

In some embodiments, the cross-sectional profile of the sheet of light may have a width parallel to the longitudinal direction of the artery that is shorter than the length of the sheet of light. In some embodiments, the cross-sectional profile of the sheet of light may have an elliptical, rectangular, triangular, or polygonal shape.

In some embodiments, the one or more transmit light guides may be configured to direct the sheet of light along a partial circumference of a limb of the subject. In some embodiments, the one or more transmit light guides may be configured to direct the sheet of light along the partial circumference of the limb for at least 40 degrees.

In some embodiments, the one or more transmit light guide may include one or more of optical facets, refractive index structures, a volume hologram, a diffractive surface relief element, or any combination thereof to direct the light from the one or more light sources into the sheet of light. In some embodiments, the one or more transmit light guides may include a planar optical waveguide, a prism, or any combination thereof configured to direct the light from the one or more light sources as the sheet of light. In some embodiments, the one or more transmit light guides may include one or more lenses configured to focus the sheet of light at a targeted focal depth. In some embodiments, the one or more transmit light guides may include one or more lenses configured to focus the sheet of light with a targeted width at the targeted focal depth. In some embodiments, the one or more transmit light guides may be configured to conform to a surface of the limb.

In some embodiments, the one or more light detectors may be configured to receive the backscattered light along a partial circumference of the limb of the subject. In some embodiments, the one or more light detectors may be a single light detector and the optical sensor may further include one or more receive light guides coupled to the single light detector. In some embodiments, each of the one or more receive light guides may be configured to collect the backscattered light and to direct the collected backscattered light towards the single light detector.

In some embodiments, the optical sensor may include multiple light detectors and multiple receive light guides, each receive light guide being coupled to a respective light detector. In some embodiments, each of the receive light guides may be configured to collect the backscattered light and direct the collected backscattered light towards its respective light detector.

In some embodiments, the optical sensor may include a processor coupled to the one or more light detectors and configured with processor-executable instructions to determine one or more cardiovascular properties based on the output from the one or more light detectors.

Further embodiments may include a method of measuring cardiovascular properties using an optical measuring device, which may include directing a sheet of light towards an artery in a subject, such that the cross-sectional profile of the sheet of light may have a length transverse to a longitudinal direction of the artery that is longer than the diameter of the artery. The method may also include receiving backscattered light that is light from the sheet of light backscattered from the artery and tissues surrounding the artery, and generating an output based on the received backscattered light. Some embodiments may further include determining one or more cardiovascular properties based on the output.

In some embodiments, the cross-sectional profile of the sheet of light may have a width parallel to the longitudinal direction of the artery that is shorter than the length of the sheet of light. In some embodiments, the cross-sectional profile of the sheet of light may have an elliptical, rectangular, triangular, or polygonal shape.

In some embodiments, directing the sheet of light towards the artery in the subject may include directing the sheet of light along a partial circumference of a limb of the subject. In some embodiments, directing the sheet of light along the partial circumference of the limb may include directing the sheet of light along the partial circumference of the limb for at least forty degrees. In some embodiments, receiving the backscattered light may include receiving the backscattered light along the partial circumference of the limb.

Further embodiments may include an optical sensor that includes means for performing functions of the operations of the embodiment methods described above.

Further embodiments may include an optical measuring device for measuring cardiovascular properties that includes an optical sensor and a processor coupled to the optical sensor. The optical sensor may include one or more light sources, one or more transmit light guides coupled to the one or more light sources and configured to direct light from the one or more light sources as a sheet of light towards an artery in a subject, such that the cross-sectional profile of the sheet of light may have a length transverse to a longitudinal direction of the artery that is longer than the diameter of the artery. The optical sensor may also include one or more light detectors configured to receive backscattered light that light from the sheet of light backscattered from the artery and tissues surrounding the artery and to generate an output based on the received backscattered light. The processor may be configured to determine one or more cardiovascular properties based on the output from the optical sensor.

In some embodiments, the cross-sectional profile of the sheet of light may have a width parallel to the longitudinal direction of the artery that is shorter than the length of the sheet of light. In some embodiments, the cross-sectional profile of the sheet of light may have an elliptical, rectangular, triangular, or polygonal shape.

BRIEF DESCRIPTION OF THE DRAWING

The accompanying drawings, which are incorporated herein and constitute part of this specification, illustrate exemplary embodiments of the claims, and together with the general description given above and the detailed description given below, serve to explain the features of the claims.

DETAILED DESCRIPTION

Figure 1:
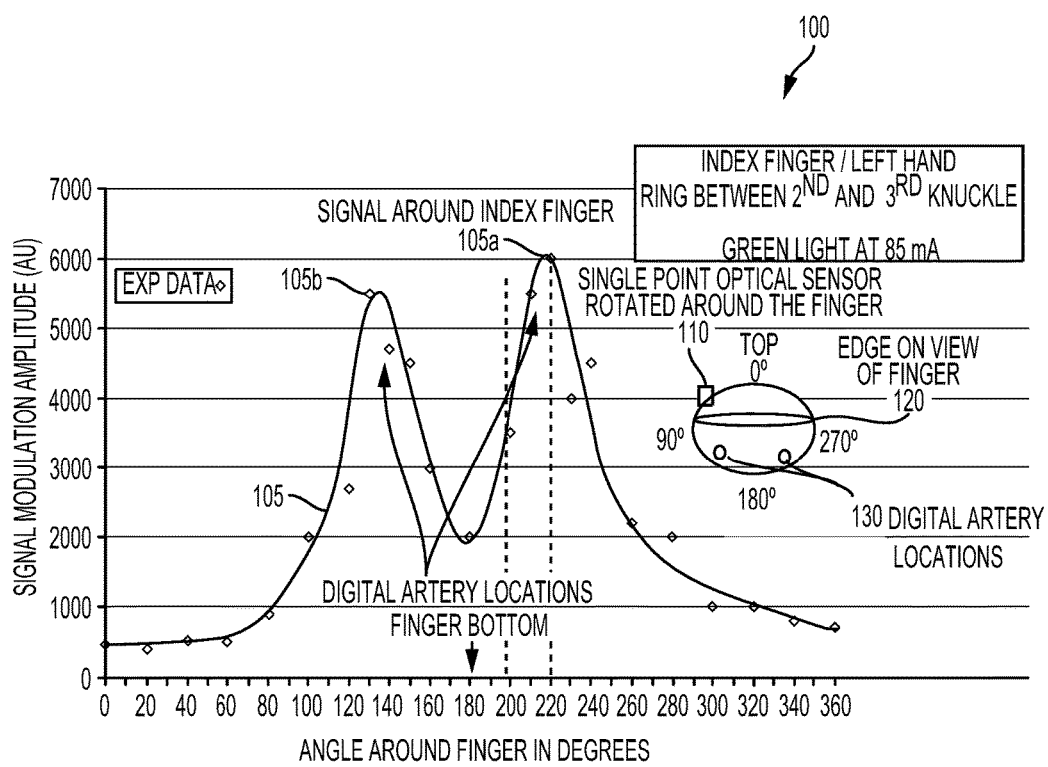
FIG. 1 illustrates in graph form how the output intensity of a conventional optical sensor may vary with angle along the circumference of an index finger.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

The term "cardiovascular properties" is used herein as a general term to refer to characteristics of a cardiovascular system including, but not limited to, arterial beat-to-beat distension, pulse transit time (PTT), pulse wave velocity (PWV), arterial stiffness, heart rate, heart rate variability, and blood pressure.

The term "optical measuring device" is used herein to refer to a physical apparatus that is configured to be placed in optical contact with the skin of a subject for taking measurements of a biometric, such as a structure that can be worn by the subject or a structure on a fixture (e.g., furniture, sports equipment, automobile fixtures, etc.). In contrast, the term "optical sensor" generally refers to a device that is configured to be placed in optical contact with the skin of a subject, such as a sensor that is wearable or can be placed on a finger, wrist or other body part or a sensor on a fixture, and that responds to a light stimulus and transmits a resulting output (as for measurement or operating a control). The term "optical contact" is used herein to mean that the emitted light from the optical measuring device is able to enter to skin of the subject and backscattered light is able to enter the optical measuring device from the skin of the subject without optical interference. Thus, a transparent structure (e.g., as a glass cover), intermediate substance (e.g., a transparent gel), or a small air gap may be interposed between the optical measuring device and the skin of the subject.

The term "limb" is used herein to refer to a finger, wrist, forearm, ankle, leg, or other body part suitable for taking measurements of cardiovascular properties.

The term "backscattered light" is used herein to refer to light from one or more light sources that has been redirected by reflection, refraction and/or reemission by tissues including arteries through an angle (e.g., 90 degrees or more) sufficient to be received by one or more light detectors of an optical measuring device.

Conventional optical measuring devices that include conventional optical sensors have been used to estimate certain cardiovascular properties, including blood pressure. For example, conventional optical sensors may include one or more light emitting diodes (LEDs) and photodiode detectors (PDs) that detect light backscattering from a small illuminated region, sometimes referred to as a light spot. Because light can propagate only short distances through human tissue, e.g., a few millimeters, the optical sensor needs to be placed in optical contact with the skin where the artery of interest is closest to the skin surface. Thus, with conventional optical sensors, a user may need to have prior knowledge or medical knowledge to determine an artery's location in order to precisely position the sensor, or the device may need to provide feedback to force the user to adjust the optical sensor to find a proper location before the user can use the optical sensor.

Light from the emitted light spot that is reflected or "backscattered" by the artery, blood particles in the artery, and other tissue, may be received by the one or more photo detectors to generate an output signal. The output may be processed to obtain an arterial pulse waveform.

Conventional optical sensors are generally configured to detect light from a spot having a cross-sectional area that is relatively small in comparison to possible movements of the artery and/or of the optical sensor relative to the artery (collectively referred to herein as arterial displacements). Arterial displacements may occur due to limb or optical sensor movements, such as twisting of a wrist, bending of a finger, slight rotation or misplacement of the optical sensor from its initial location or any combination thereof. Arterial displacements may range up to several millimeters or more, and may result in movement artifacts, or aberrations, in the output of a conventional optical sensor. The accuracy of cardiovascular property measurements based on the output of optical sensors may depend significantly upon arterial displacement.

For example, FIG. 1 illustrates in graph form how the output intensity of a conventional optical sensor 110 may vary with angle along the circumference of an index finger 120. A conventional optical sensor 110 may detect and output the intensity of backscattered light from a small illuminated region (or spot) reflected by an artery or other tissue. The intensity plots may be obtained by measuring the output of the conventional optical sensor 110 as the optical sensor is rotated incrementally around the circumference of an index finger 120.

As shown in the graph 100, a zero (0) degree rotation corresponds to the optical sensor 110 being placed on top of an index finger. The signal intensity curve 105 includes peaks 105a and 105b within narrow bands at about 220 degrees and 140 degrees, respectively. These narrow bands correspond to locations 130 on the surface of the index finger 120 at which two arteries may be closest to the sensor 110 and light scattering or absorption are at the maximum. A consequence of the output of the conventional optical sensor 110 peaking within these narrow bands is that small rotations of the optical sensor about the finger may result in significant movement artifacts in the sensor output. As a result, optical measuring devices that measure cardiovascular properties using conventional optical sensors that detect light from a spot having a cross-sectional area that is relatively small in comparison to possible arterial displacements are generally not reliable. While the graph 100 in FIG. 1 illustrates measurements of a convention optical sensor including a single spot of light, the problem illustrated in the graph 100 may also occur when a conventional optical sensor includes multiple spots of light and corresponding sensors.

Figure 11:
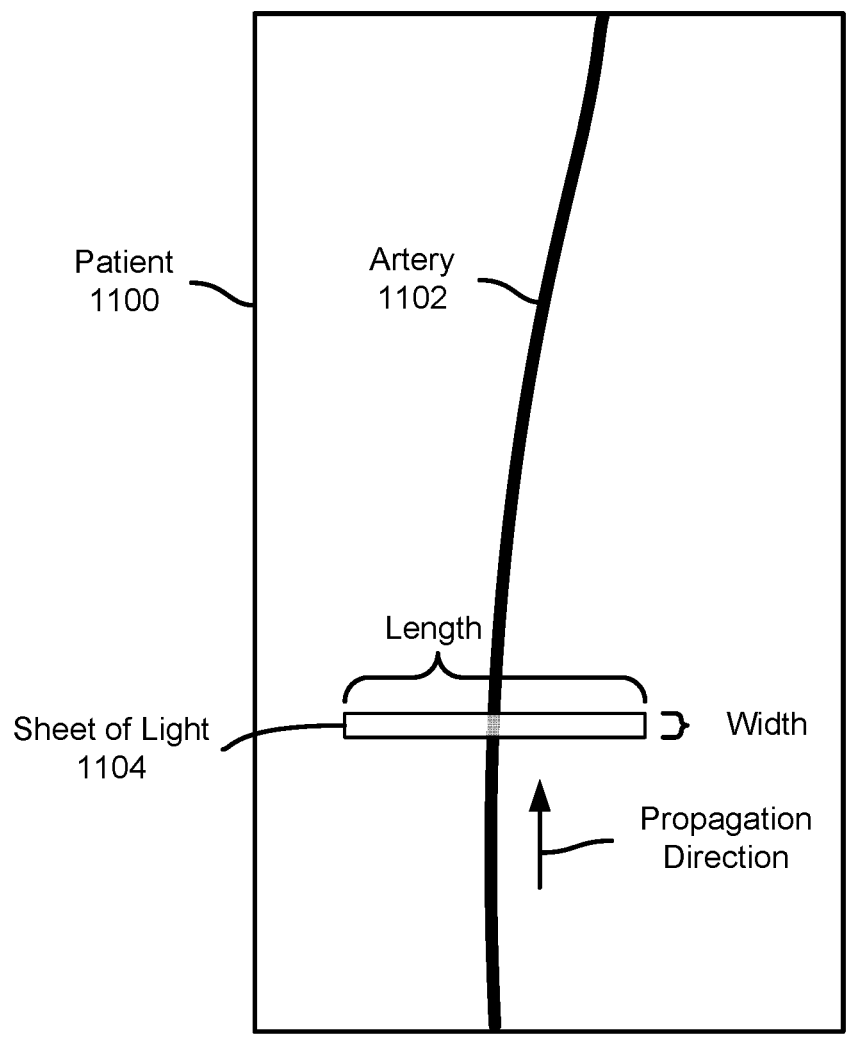
FIG. 11 illustrates an example cross-section of a sheet of light according to some embodiments.

The various embodiments include an optical sensor for use in an optical measuring device configured to obtain measurements of cardiovascular properties. In particular, the various embodiments may include an optical sensor configured to emit light that with a cross-sectional profile in which one axis is longer than a second axis, referred to herein as a "sheet of light," into a limb of a subject and to receive backscattered light and generate an output from the received backscattered light for use in measuring various cardiovascular properties. The term "sheet of light" is used herein as a shorthand reference to emitted light having an asymmetric cross-section, (i.e., one axis transverse to the direction of propagation) is longer that the perpendicular axis also transverse to the propagation direction. The longer axis of the sheet of light is sometimes referred to herein as the "length of the sheet of light," while the shorter transverse axis is sometimes referred to herein as the "width of the sheet of light." The term "sheet of light" is not intended to be further limiting and encompasses emitted light with a cross-sectional profile of any shape, including elliptical, rectangular, triangular, polygonal, etc. One example of a sheet of light 1104 projected onto a patient 1100 having an asymmetric cross-section is shown in FIG. 11, where the sheet of light 1104 is projected transverse to the propagation direction within the artery 1102 and has a length that is greater than its width.

By emitting a sheet of light, the various embodiments enable the optical sensor to be positioned on a limb of a subject so that the sheet of light is oriented approximately perpendicular to the longitudinal direction of an artery. So oriented, the length of the sheet of light increases the likelihood that emitted light will illuminate the artery when the person applying the optical sensor does not have prior knowledge of the location of the artery in the limb. In some embodiments, the optical sensor may be configured such that the length of the sheet of light may be equal to or longer than a minimum arterial displacement, an average arterial displacement, or a maximum arterial displacement so that the artery may remain within an illuminated volume despite such displacement. For example, in some embodiments in which the optical sensor is configured to be positioned on a finger, the length of the sheet of light may be several millimeters (mm), e.g., up to 10 mm. In some embodiments in which the optical sensor is configured to be positioned on a wrist, the length of the sheet of light may extend up to 1 centimeter (cm) or more. In some embodiments, the width of the sheet of light may range between 30 microns (μm) to 1 mm. For example, in some embodiments, the width of the sheet of light may be equal to twenty percent or less of the length of the sheet of light.

In some embodiments, the optical sensor may be configured so that the sheet of light has a cross-section with a transverse axis that extends for a range of rotational degrees about a location on the circumference of the limb (e.g., finger, wrist, ankle, etc.) at which the artery of interest is closest to the skin and the intensity of the sensor output peaks. In some embodiments, the optical sensor may be configured such that the sheet of light may be emitted so that the transverse axis extends along a partial circumference of the limb. In some embodiments, the optical sensor may be configured such that the transverse axis of the sheet of light may extend around the entire circumference of the limb.

When positioned on a limb so that the long axis of the emitted light is roughly perpendicular to the long axis of an artery, the optical sensor may be configured such that the light is emitted as a wide but thin sheet of light ensures that some of the light energy will be applied to the artery even if the artery and/or the optical sensor shifts. In various embodiments, the optical measuring device may be configured to measure characteristics of a subject's cardiovascular system including, but not limited to, arterial distension, pulse transit time (PTT), pulse wave velocity (PWV), arterial stiffness, heart rate, heart rate variability, and blood pressure.

The various embodiments may provide an optical measuring device that is able to provide measurements of cardiovascular properties in a manner that minimizes or avoids artifacts from arterial displacements. Thus, optical measuring devices of various embodiments may be placed on the subject without requiring a precise knowledge of the location of the artery.

Figure 2:
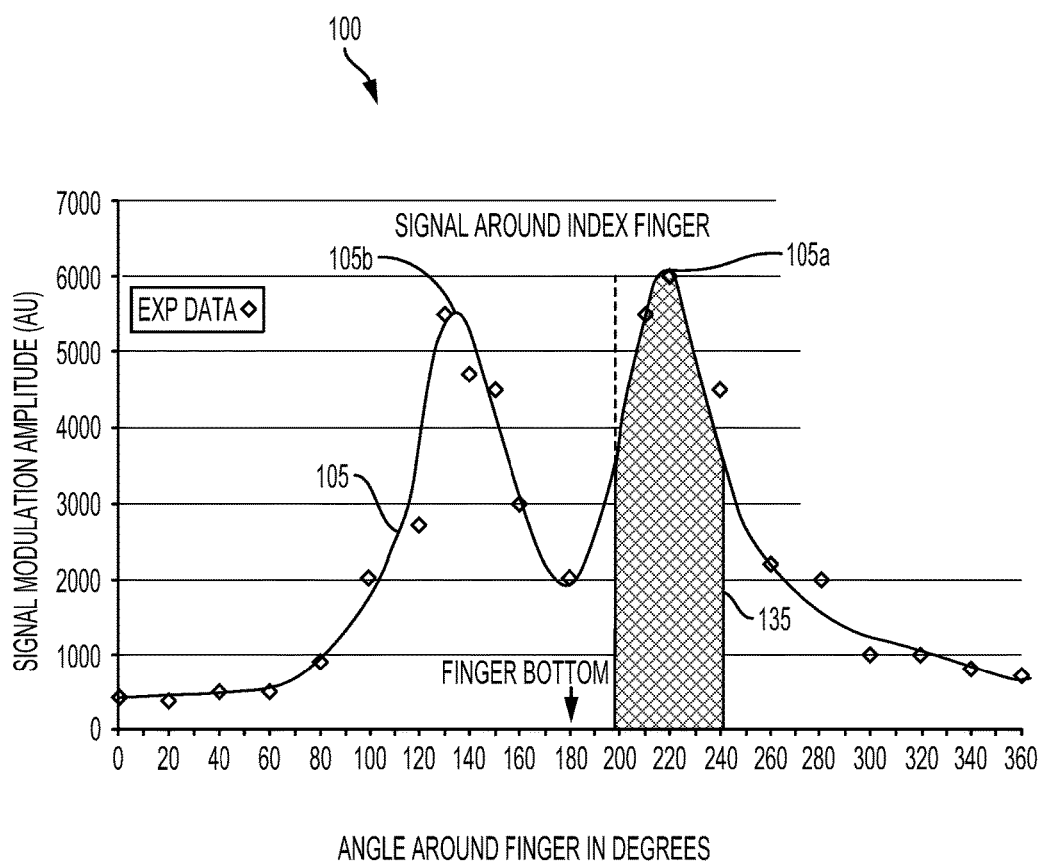
FIG. 2 illustrates in graph form how an optical sensor according to various embodiments may compensate for movement artifacts by directing a sheet of light across an artery of interest.

FIG. 2 illustrates in graph form how an embodiment optical sensor may compensate for movement artifacts by directing a sheet of light across an artery of interest. FIG. 2 is similar to the graph 100 of FIG. 1, which was the signal intensity curve 105 of a conventional optical sensor.

However, FIG. 2 illustrates that by directing a sheet of light across the artery of interest, an embodiment optical sensor may receive backscattered light and generate an output in which the signal intensity of the received backscattering of the sheet of light is integrated across the length of the sheet of light. The sheet of light may be configured so that the long axis of the light cross-section extends approximately 40 degrees about the circumference of an index finger or other limb. Thus, even as the optical sensor rotates around the finger, the optical sensor may continue to receive backscattered light resulting from the artery reflecting a portion of the sheet of light. In addition, by employing an embodiment optical sensor that emits and receives backscattering of a sheet of light, the optical sensor may be placed on the patient without having precise or any knowledge of the location of the artery with the patient. For example, in some embodiments, the optical sensor may be integrated into a wearable optical measuring device, such as a watch, a medical patch, a wristband, smart clothing, etc. Although the user may not be aware of the location of the artery, it may be sufficient that user knows that the optical sensor (e.g., a watch) is worn on their wrist, avoiding the need to require instructional documentation that informs the user regarding proper placement of the optical sensor (e.g., a watch) on the body.

Figure 3A:
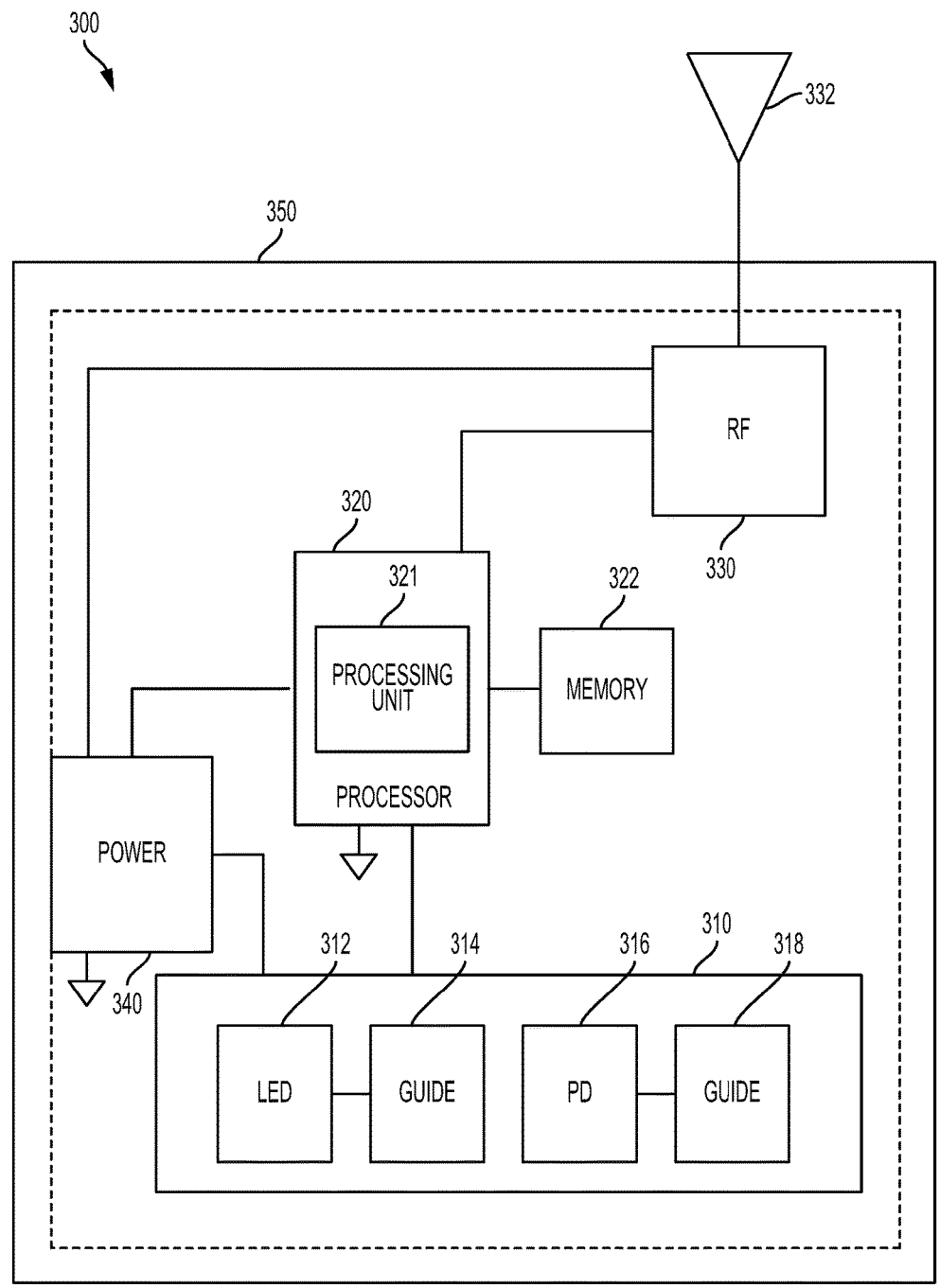
FIG. 3A illustrates components of an optical measuring device including a optical sensor according to some embodiments.

FIG. 3A illustrates example components of an optical measuring device 300 including an optical sensor 310 according to some embodiments. An optical measuring device 300 may include an optical sensor 310, a processor 320, memory 322, a radio frequency (RF) processor 330 coupled to an antenna 332, and a power supply 340.

The optical sensor 310 may include one or more light sources 312 coupled to one or more transmit light guides 314 configured to direct light from the one or more light sources into a sheet of light. In some embodiments, the one or more light sources 312 may inject light into the one or more transmit light guides 314, which directs the light out of the transmit light guide 314 as a sheet of light towards the subject's limb. In various embodiments, the one or more transmit light guides 314 may include various optical turning features for directing the light from the one or more light sources 312 into a sheet of light, including without limitation, optical turning facets, refractive index structures, volume holograms, and/or diffractive surface relief elements, as described in more detail with reference to FIGS. 4A-8B.

The optical sensor 310 may further include one or more light detectors 316 configured to receive backscattered light and generate an output proportional to the received backscattered light. As described, energy from the sheet of light may be backscattered by an artery and blood particles in the artery, as well as tissues surrounding the artery. Thus, the output generated by the one or more light detectors 316 may provide a measure of the light absorption of the artery and tissue surrounding the artery based on intensity of backscattered light that may be used to measure various cardiovascular properties.

In some embodiments, one or more light detectors 316 may be arranged on or along either or both sides of the one or more transmit light guides 314 to receive the backscattered light. In some embodiments, the one or more light detectors 316 may be integrated within the one or more transmit light guide 314 itself. In embodiments that include multiple light detectors, the outputs of the respective detectors 316 may be combined, averaged, or used individually to identify a maximum or minimum in order to determine different characteristics or measurements from received backscattered light. In some embodiments, each of the one or more light detectors 316 may be coupled to one or more receive light guides 318 that is/are configured to collect backscattered light along a circumference of a limb and to direct the collected light towards one or more light detectors. In some embodiments, the one or more light detectors 316 may be photodiode detectors.

The optical sensor 310 may be coupled to the processor 320 so that the processor receives the output of the one or more light detectors 316. In some embodiments, the processor 320 may be dedicated hardware specifically adapted to perform a variety of functions for the optical measuring device 300. In some embodiments, the processor 320 may be or include a programmable processing unit 321 that may be programmed with processor-executable instructions. In some embodiments, the processor 320 may be a programmable microprocessor, microcomputer or multiple processor chip or chips that can be configured by software instructions to perform a variety of functions of the optical measuring device 300. In some embodiments, the processor 320 may be a combination of dedicated hardware and a programmable processing unit 321.

In some embodiments, the memory 322 may store processor-executable instructions and/or outputs from the optical sensor 310. In some embodiments, the memory 322 may be volatile memory, non-volatile memory (e.g., flash memory), or a combination thereof. In some embodiments, the memory 322 may include internal memory included in the processor 320, memory external to the processor 320, or a combination thereof.

In some embodiments, the processor 320 may be coupled to the one or more light sources 312, the one or more light detectors 316, or any combination thereof. In some embodiments, the processor 320 may be configured to selectively control when one or more light sources 312 and a light detector 316 are activated (e.g., turned on and off). In some embodiments, the processor 320 may independently control the one or more light sources 312 and the light detector 316. For example, in some embodiments, the processor 320 may control activation of the one or more light sources 312 and the detector 316, such that there may be a time delay between when the one or more light sources 312 is activated and when the light detector 316 is activated.

In some embodiments, the processor 320 may be further configured to receive and process the output of the one or more light detectors 316. For example, the processor 320 may be configured to analyse the output of the light detectors 316 and produce a measurement of one or more cardiovascular properties.

In some embodiments, the processor 320 may be configured to estimate one or more cardiovascular properties based on the output of the optical sensors 310. For example, by including two optical sensors 310a, 310b within the finger sleeve, the processor 320 may be able to measure a pulse transit time (PTT) between the two optical sensor locations. Knowing the distance between the two optical sensor locations, the processor 320 may also be able to calculate a pulse wave velocity (PWV) based on the PTT measurement.

In some embodiments, the processor 320 may be coupled to RF processor 330 in order to communicate sensor output and/or measured cardiovascular properties via an antenna 332 to a remote computing device (not shown) for presentation through a display or other output device. The RF processor 330 may be a transmit-only or a two-way transceiver processor. For example, the RF processor 330 may include a single transceiver chip or a combination of multiple transceiver chips for transmitting and/or receiving signals. The RF processor 330 may operate in one or more of a number of radio frequency bands depending on the supported type of communications.

The processor 320 may be configured to transmit measured or calculated information, such as measured values of the cardiovascular properties or the output from the optical sensor 310, to a remote computing device (not shown) for recording or display. Such a remote computing device may be any of a variety of computing devices, including but not limited to a processor in smart clothing, cellular telephones, smart-phones, web-pads, tablet computers, Internet enabled cellular telephones, wireless local area network (WLAN) enabled electronic devices, laptop computers, dedicated healthcare electronic devices, personal computers, and similar electronic devices equipped with at least a processor and a communication resource to communicate with the RF processor 330. Measured and/or calculated information may be transmitted from the optical measuring device 300 to a remote computing device over a wireless link using Bluetooth®, Wi-Fi® or other wireless communication protocol.

The optical sensor 310, the processor 320, the RF processor 330, and any other electronic components of the optical measuring device 300 may be powered by a power supply 340. In some embodiments, the power supply 340 may be a battery, a solar cell, or other type of energy harvesting power supply.

In various embodiments, some or all of the components of the optical measuring device (e.g., 310, 320, 330, and 340) may be supported by a back support 350. In some embodiments, the back support 350 may be implemented with flexible materials so that the optical measuring device 300 may wrap around or otherwise conform to the surface of the subject, such as a finger, wrist, or other limb. In some embodiments, the back support 350 may be rigid. In some embodiments, the back support 350 may provide flexibility in one portion of the optical measuring device 300, while the rest of the device has a rigid structure. In some embodiments, the optical sensor 310 or any component thereof (e.g., one or more light sources 312, one or more transmit light guides 314, and/or one or more light detectors 316) may be configured to be flexible. For example, in some embodiments, the optical sensor 310 or any component thereof may be embedded in an elastomer.

In some embodiments, the optical measuring device 300 may be configured in the form of, or incorporated into, a patch, a finger sleeve, a wrist cuff, a finger ring, band of a wrist watch, back case of a wrist watch, and/or other form of apparel (i.e., clothing that includes an embodiment of the optical measuring device 300). However, the various embodiments are not limited to implementations that are directly worn by a subject, and may include configurations that place the optical sensor against the skin of the subject. For example, in some embodiments, the optical measuring device 300 may be incorporated into safety belts, steering wheels, armrests, seats and other structures in an automobile, train, airplane, or other vehicle, and configured so that the optical sensor(s) come in optical contact with the skin of a subject. As another example, in some embodiments, the optical measuring device 300 may be incorporated into smart furniture and configured so that the optical sensor(s) come in optical contact with the skin of a subject. As a further example, in some embodiments, the optical measuring device 300 may be incorporated into athletic equipment, such as helmets, racket handles, wrist or headbands, shoes, socks, handle bars, etc., and configured so that the optical sensor(s) come in optical contact with the skin of a subject.

Figure 3B:
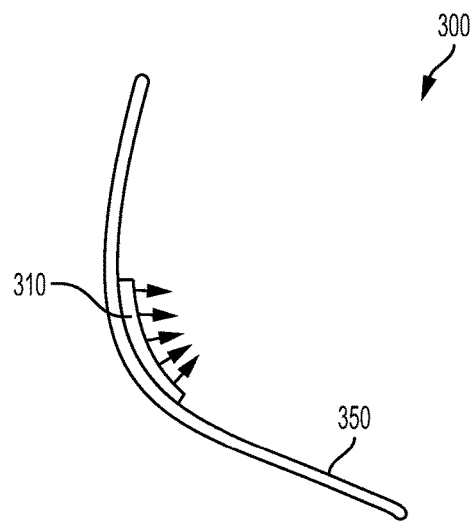
FIG. 3B illustrates a side view of an optical measuring device according to some embodiments.

FIG. 3B illustrates a side view of an optical measuring device 300 according to some embodiments. As illustrated, the optical sensor 310 may adhere to the back support 350, which is configured in the form of a patch. When the patch is applied to the skin surface of a limb of a subject, the optical sensor 310 may be controlled by the processor (e.g., 320) to direct a sheet of light (shown by arrows) into the limb of the subject and to receive and generate an output from the backscattered light for use in measuring various cardiovascular properties.

Figure 3C:
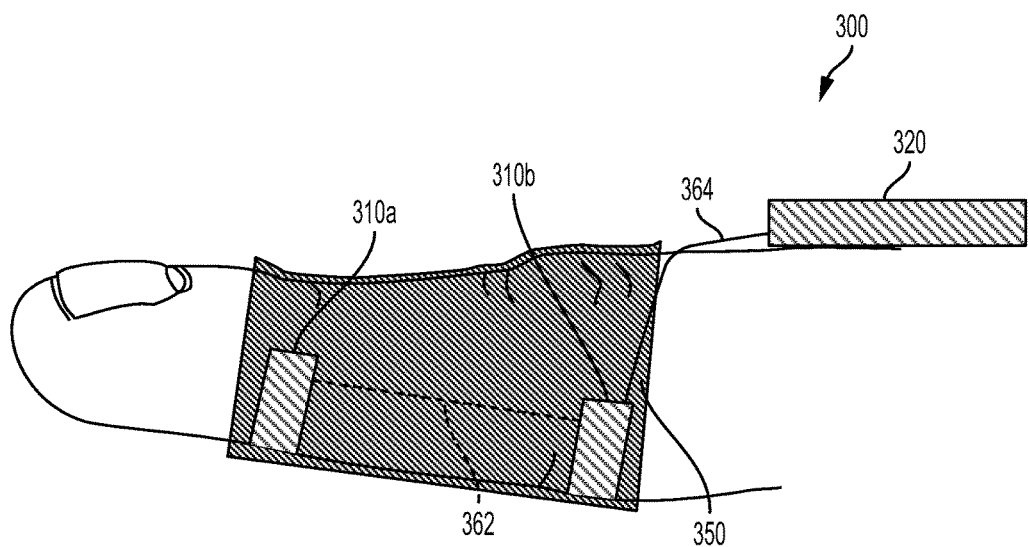
FIG. 3C illustrates an optical measuring device according to some embodiments.

FIG. 3C illustrates an optical measuring device 300 according to an embodiment suitable for deployment on a finger of a subject. In the embodiment illustrated in FIG. 3C, the optical measuring device 300 includes two optical sensors 310a, 310b (collectively 310) arranged on an interior surface of the back support 350 in the form of a finger sleeve, although other embodiments may include fewer or more sensors. The optical sensors 310 may be coupled to the processor 320 by flexible wired connections 362 and 364 to accommodating bending in the finger sleeve when applied and while worn.

Figure 4A:
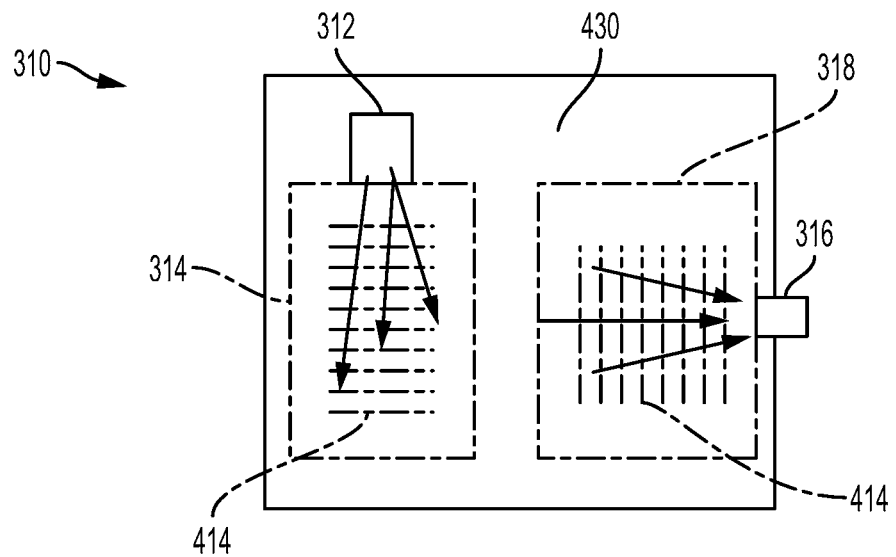
FIGS. 4A and 4B illustrate a structure of an optical sensor according to a first embodiment.
Figure 4B:
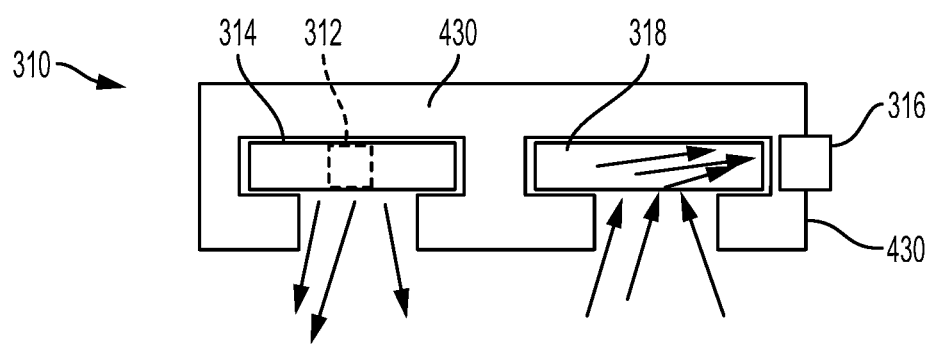

FIGS. 4A and 4B illustrate a first embodiment for arranging one or more light source 312, one or more transmit light guides 314, one or more light detectors 316 and one or more receive light guides 318 of an optical sensor 310. In particular, FIG. 4A illustrates a bottom view of an optical sensor 310 directed towards a surface of a limb. FIG. 4B is a cross-sectional view of the optical sensor 310.

As illustrated in these figures, the optical sensor 310 may include one or more light sources 312 coupled to one or more transmit light guides 314 and one or more light detectors 316 coupled to one or more receive light guides 318. These components may be supported on a flexible substrate 430 that may serve as a light baffle between the one or more light sources and light detection components.

In some embodiments, the one or more light sources 312 may be a light emitting diode (LED) that generates light of a particular wavelength. For example, the LED may generate visible light having a wavelength corresponding to green light. In some embodiments, the one or more light sources 312 may be or include a laser. For example, a laser light source may be a vertical-cavity surface-emitting laser (VCSEL) that generates a light beam having a wavelength in the infrared (IR) region. In some embodiments, the one or more light sources 312 may include optical fibers that direct light from any other suitable light source.

The one or more light sources 312 inject light into the one or more transmit light guides 314. In some embodiments, the light from the one or more light sources 312 is transmitted through a light coupler or other optical structure for injecting the light into the one or more transmit light guides 314. As the light from the one or more light sources 312 propagates across the one or more transmit light guides 314, the optical turning features 414 arranged within the one or more light guides 314 may direct the light out of the one or more transmit light guide 314 as a uniform sheet of light that will be directed towards a partial circumference of the limb of a subject when the optical sensor 310 is positioned on the limb. The one or more transmit light guides 314 may be positioned and configured within the optical sensor 310 so that the length of the sheet of light is oriented perpendicular to a longitudinal direction of arteries when the optical sensor 310 is positioned on a limb of a subject, and extend along a partial circumference of the limb.

Light backscattered by the artery, blood particles within the artery and the surrounding tissue may be collected by the one or more receive light guides 318. As the one or more receive light guides 318 collect the backscattered light along the circumference of the limb on which the sheet of light was emitted, the optical turning features 414 arranged within the receive light guide 318 may direct the collected light towards the one or more light detectors 316. The one or more light detectors 316 detect the backscattered light collected along the circumference of the limb and generate an output signal or signals communicated to a processor 320 for processing as described with reference to FIG. 3A.

As shown in FIGS. 4A and 4B, the one or more light detectors 316 and the optical turning features 414 of the one or more receive light guide 318 may be offset clockwise 90 degrees relative to the orientation of the optical turning features 414 of the one or more transmit light guides 314.

In some embodiments, the optical turning features 414 of the transmit and receive light guides, respectively, may be implemented as an array of optical turning facets. In some embodiments, the optical turning facets may each have a symmetric shape, such as a V-groove. In some embodiments, the optical turning facets may each have an asymmetric shape, such as a saw-tooth. The optical turning facets may each include a sidewall angled at about 45 degrees relative to a planar surface of the waveguide to a depth of about 2 to 20 microns. In some embodiments, the distance between respective turning facets may range, for example, between approximately 10 to 100 microns. In some embodiments, the distance between respective turning facets may increase with the length of the one or more transmit light guides 314 away from the one or more light sources in order to provide a more uniform emission intensity output.

In some embodiments, the optical turning features 414 of the one or more transmit light guides 314 and one or more receive light guides 318 may be implemented as an refractive index structure embedded within the respective light guides 314, 318 for coupling light into and out of the light guides. For example, such structures may include those known in the art for realizing Bragg filters or implementing holographic optical elements. In some embodiments, refractive index structures may be included and configured to complement facets and/or V-grooves in the one or more transmit light guide 314 and/or the one or more receive light guide 318.

In some embodiments, the optical turning features 414 of the transmit and receive light guides 314, 318 may be implemented as volume holograms and/or diffractive surface relief elements or gratings. In some embodiments, the optical turning features 414 of the transmit and receive light guides 314, 318 may include various combinations of two or more of the different types of optical turning features 414, including those discussed above.

In some embodiments, the one or more transmit light guides 314 and the one or more receive light guides 318 may be implemented as optical planar waveguides of a transparent material, such as acrylic and polycarbonate materials.

In some embodiments, the one or more transmit light guides 314, the one or more receive light guides 318, or both, may be equipped with one or more lenses (not shown in FIGS. 4A and 4B). For example, the transmit light guide 314 may be configured with one or more lenses to focus the sheet of light at a targeted focal depth and/or beam size. In some embodiments, the lens may be configured to focus the sheet of light emitted from the transmit light guide 314 towards a focal depth that corresponds to an expected location of the artery of interest. In some embodiments, the lens may be configured to focus the sheet of light to have a targeted width in a direction parallel to the longitudinal direction of the artery. The receive light guide 318 may be equipped with a lens to focus the backscattered light towards the receive light guide 318.

In some embodiments, the lens may include one or more fixed lenses, such as a cylindrical lens. In some embodiments, the lens may include one or more dynamic lenses that may be configured to provide variable control over the direction (e.g., left or right) and/or depth of the sheet of light emitted from the optical sensor. In some embodiment, the dynamic lens may be controllable by the processor and/or dedicated hardware. In other embodiments, a dynamic lens may be configured as an elastomer lens in a piezo-ring, which may also be realized as a deformable reflective device. In some embodiments, a dynamic lens may be realized using a liquid crystal, phase element.

Figure 5A:
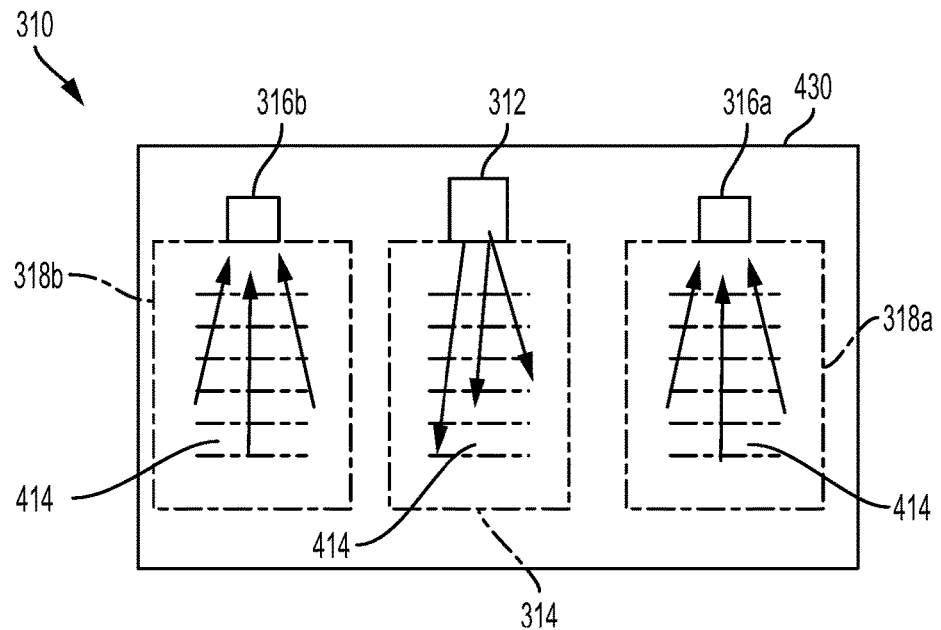
FIGS. 5A and 5B illustrate a structure of an optical sensor according to a second embodiment.
Figure 5B:
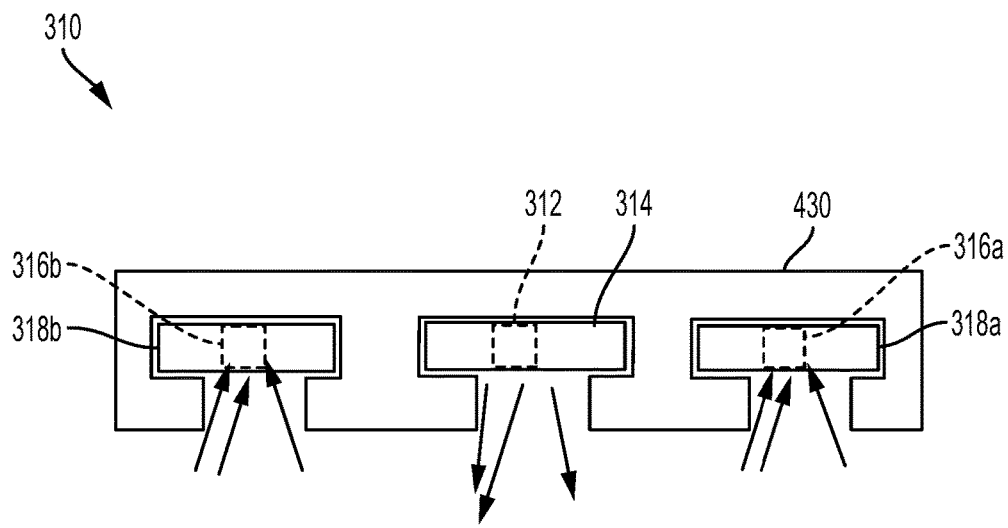

FIGS. 5A and 5B illustrate a second embodiment for arranging the one or more light sources 312, one or more transmit light guides 314, one or more light detectors 316 and one or more receive light guides 318 of an optical sensor 310. FIG. 5A illustrates a bottom view of an optical sensor 310 directed towards a surface of a limb. FIG. 5B is a cross-sectional view of the optical sensor 310. As illustrated, the optical sensor 310 may include one or more light sources 312 coupled to one or more transmit light guides 314, a first light detector 316a coupled to a first receive light guide 318a, and, optionally, a second light detector 316b coupled to a second receive light guide 318b. These components may be supported on a flexible substrate 430 that may serve as a light baffle between the one or more light sources and light detection components.

The embodiments illustrated in FIGS. 5A and 5B differ from the embodiments illustrated in FIGS. 4A and 4B in that the one or more light detectors 316a, the second receive light guide 318b and the optical turning features 414 may be oriented parallel to the orientation of the one or more transmit light guides 314 and the optical turning features 414. This parallel configuration may facilitate improvements in signal-to-noise ratio of the optical sensor and may enable both light emitter and light detectors to be mounted on the same planar structure.

The embodiments illustrated in FIGS. 5A and 5B may optionally include a second light detector 316b and a second receive light guide 318b having optical turning features 414. This optional configuration may facilitate detection of backscattered light on either side of the emitted sheet of light. The outputs of the respective light detectors 316a, 316b may be combined, averaged, or used to identify a maximum or minimum in order to obtain an output corresponding to the received backscattering of the sheet of light.

Figure 6:
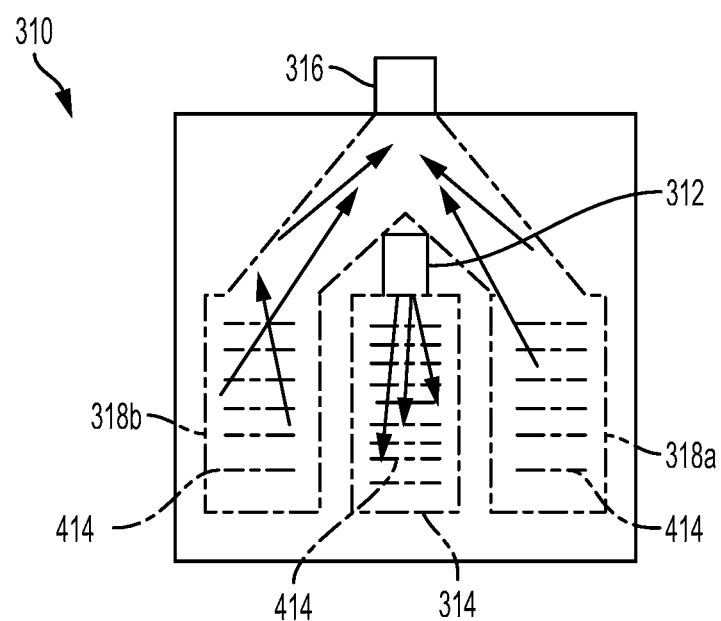
FIG. 6 illustrates a structure of an optical sensor according to a third embodiment.

FIG. 6 illustrates a third embodiment for arranging the one or more light sources 312, one or more transmit light guides 314, a single light detector 316 and one or more receive light guides 318 of an optical sensor 310. The third embodiment of the optical sensor 310 illustrated in FIG. 6 differs from the second embodiment illustrated in FIGS. 5A and 5B in that the backscattered light collected by the receive light guides 318a and 318b may be directed towards a single light detector 316. For example, FIG. 6 illustrates a bottom view of an optical sensor 310 directed towards a surface of a limb. As illustrated, the optical sensor 310 may include one or more light sources 312 coupled to one or more transmit light guides 314 and a single light detector 316 coupled to two receive light guides 318a, 318b. These components may be supported on a flexible substrate 430 that may serve as a light baffle between the one or more light sources and light detection components.

The receive light guides 318a, 318b and the respective optical turning features 414 may be oriented in parallel to the orientation of the transmit light guide 314 and the optical turning features 414 of the transmit light guide 314.

The single light detector 316 may receive the backscattered light collected along the partial circumference of the limb and generate an output from which a signal containing a pulse waveform of the artery may be obtained using the backscattered light from both of the receive light guides 318a, 318b. Thus, the two (or more) receive light guides 318a, 318b may be configured to combine received light and direct such light on the single light detector 316. The output may be communicated to the processor (e.g., 320 of FIG. 3A).

Figure 7A:
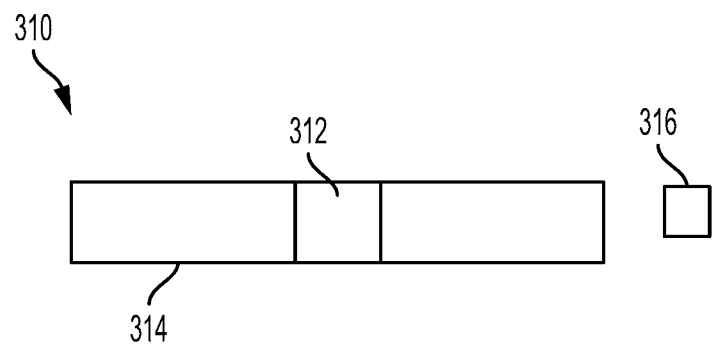
FIGS. 7A and 7B illustrate a structure of an optical sensor according to a fourth embodiment.
Figure 7B:
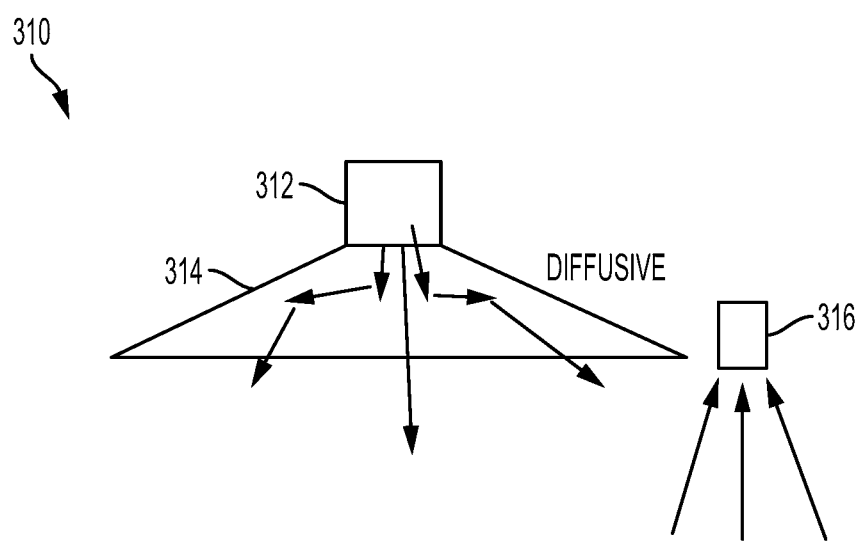

FIGS. 7A and 7B illustrate a fourth embodiment for arranging the one or more light sources 312, one or more transmit light guides 314, one or more light detectors 316 and one or more receive light guides 318 of an optical sensor 310. FIGS. 7A and 7B illustrates a top view and a cross-sectional view, respectively, of the optical sensor 310.

The one or more light sources 312 may inject light into the one or more transmit light guides 314 having an optical medium capable of diffusing the light. As the light from the one or more light sources 312 propagates through the transmit light guide 314, the optical medium diffuses the light into a sheet of light that is emitted towards a partial circumference of the limb. The length of the sheet of light may be oriented perpendicular to a longitudinal direction of the artery and extend along a partial circumference of the limb.

The one or more transmit light guides 314 may be configured as a triangular prism through which the light is injected at the apex of the prism and emits a sheet of light out of the rectangular base of the prism. The length of the long-axis of the cross-section of the sheet of light may be equal to the length of the rectangular base of the prism.

The one or more light detectors 316 may receive the backscattered light collected along the partial circumference of the limb and generate an output that may be communicated to the processor 320 for processing as described with reference to FIG. 3A.

Figure 8A:
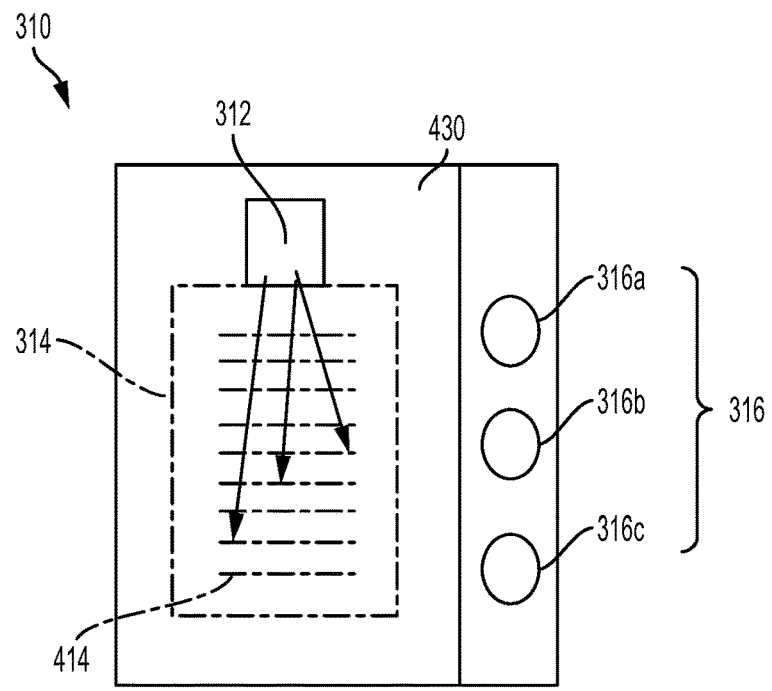
FIGS. 8A and 8B illustrate a structure of an optical sensor according to a fifth embodiment.
Figure 8B:
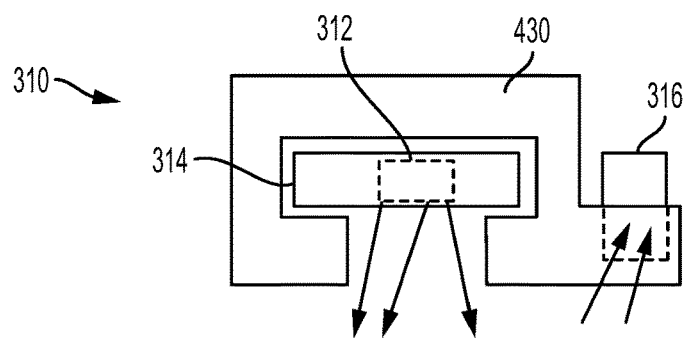

FIGS. 8A and 8B illustrate a first embodiment for arranging the one or more light sources 312, one or more transmit light guides 314, two or more light detectors 316, and one or more receive light guides 318 of an optical sensor 310. In particular, FIG. 8A illustrates a bottom view of an optical sensor 310 directed towards a surface of a limb. FIG. 8B is a cross-sectional view of the optical sensor 310. As illustrated in these figures, the optical sensor 310 may include one or more light sources 312 coupled to one or more transmit light guides 314, and two or more light detectors 316a, 316b, and 316c. These components may be supported on a flexible substrate 430 that may serve as a light baffle between the one or more light sources and two or more light detection components.

The light detectors 316a, 316b, and 316c may be distributed along either or both sides of the one or more transmit light guides 314. As illustrated, for example, the light detectors 316a, 316b, and 316c may be spaced apart in equal distances along a side of a single transmit light guide 314. In this configuration, each of the individual light detectors 316a, 316b, and 316c may receive a portion of the backscattered light along the partial circumference of the limb and generates a corresponding output.

In implementations in which multiple light detectors 316a, 316b, and 316c are used for detection of backscattered light, the outputs of the respective detectors may be combined, averaged, or used to identify a maximum or minimum in order to obtain an integrated output corresponding to the backscattered light along the length of the partial circumference. In some embodiments, the corresponding output from each light detector 316a, 316b, and 316c may be communicated to the processor (e.g., 320 of FIG. 3A) to generate an output. In some embodiments, an adder or other mixing logic may be employed to combine the respective outputs of the individual light detectors 316a, 316b, and 316c and subsequently communicate an integrated output to the processor.

Figure 9:
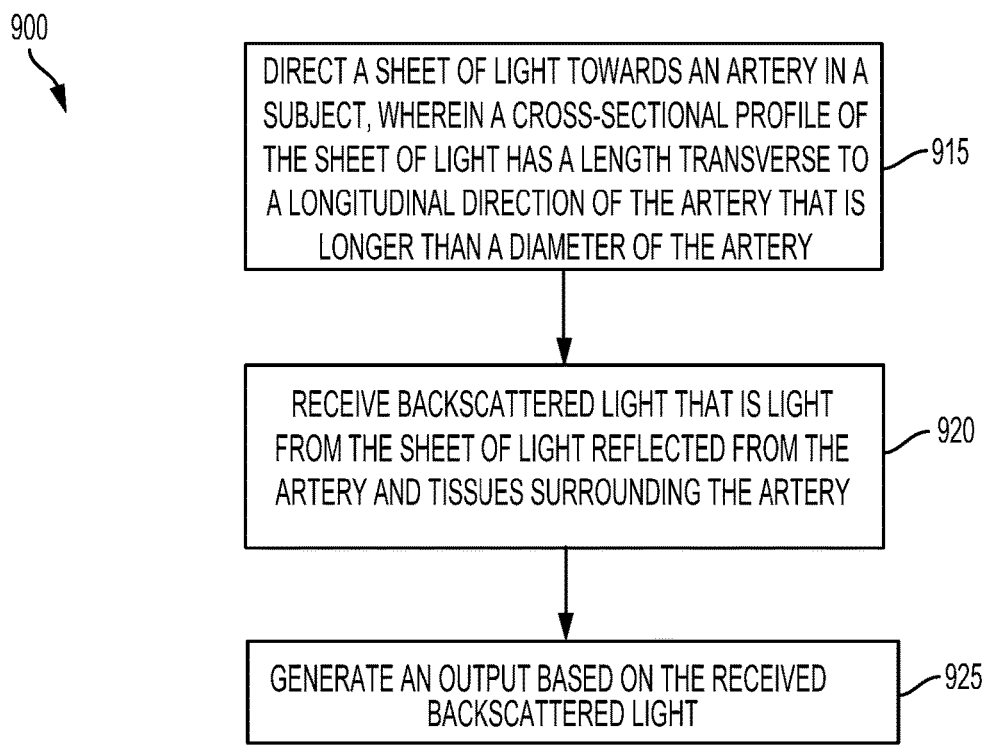
FIG. 9 illustrates a method of measuring cardiovascular properties using an optical sensor according to some embodiments.

FIG. 9 illustrates a method 900 of using an optical sensor for obtaining measurements of cardiovascular properties in an optical measuring device positioned on a subject according to various embodiments.

In block 915, the one or more transmit light guides (e.g., 314) directs light from one or more light sources (e.g., 312) as a sheet of light towards an artery in the subject. The sheet of light may have a cross-sectional profile of a sheet of light that has a length transverse to a longitudinal direction of the artery that is longer than the diameter of the artery. In some embodiments, the transmit light guide may be configured to direct the sheet of light along a partial circumference of a subject's limb when the optical measuring device is deployed on the subject's limb. By directing light along a partial circumference of the limb, some portion of the sheet of light may illuminate a location at which the artery is closest to a surface of the limb when the optical measuring device is placed on the subject, obviating a need to precisely locate the optical measuring device on the limb. Further, by directing a sheet of light along a partial circumference of a subject's limb, the optical measuring device may continue to obtain optical information relative to an artery of interest despite limited arterial displacements relative to the optical sensor.

In block 920, one or more light detectors (e.g., 316) receive backscattered light, which is light from the sheet of light that is backscattered from the artery and tissues surrounding the artery. In some embodiments, the one or more light detectors (e.g., 316) receive backscattered light along the partial circumference of the limb from the artery and the surrounding tissues that reflect the sheet of light. In some embodiments, the one or more light detectors may be coupled to a respective receive light guide which collects the backscattered light along the partial circumference of the limb and directs the collected backscattered light towards the respective light detector.

In block 925, the one or more light detectors (e.g., 316) may generate an output corresponding to a received amount of backscattered light. For example, one or more light detectors 316 may be configured to receive backscattered light and generate an output proportional to the received backscattered light. As described, energy from the sheet of light may be backscattered by an artery and blood particles in the artery, as well as tissues surrounding the artery. Thus, the output generated by the one or more light detectors 316 may provide a measure of the light absorption of the artery and tissue surrounding the artery based on intensity of backscattered light that may be used to measure various cardiovascular properties. In some embodiments that include multiple light detectors, the outputs of the respective detectors may be combined, averaged, or used individually to identify a maximum or minimum in order to determine different characteristics or measurements from received backscattered light.

Figure 10:
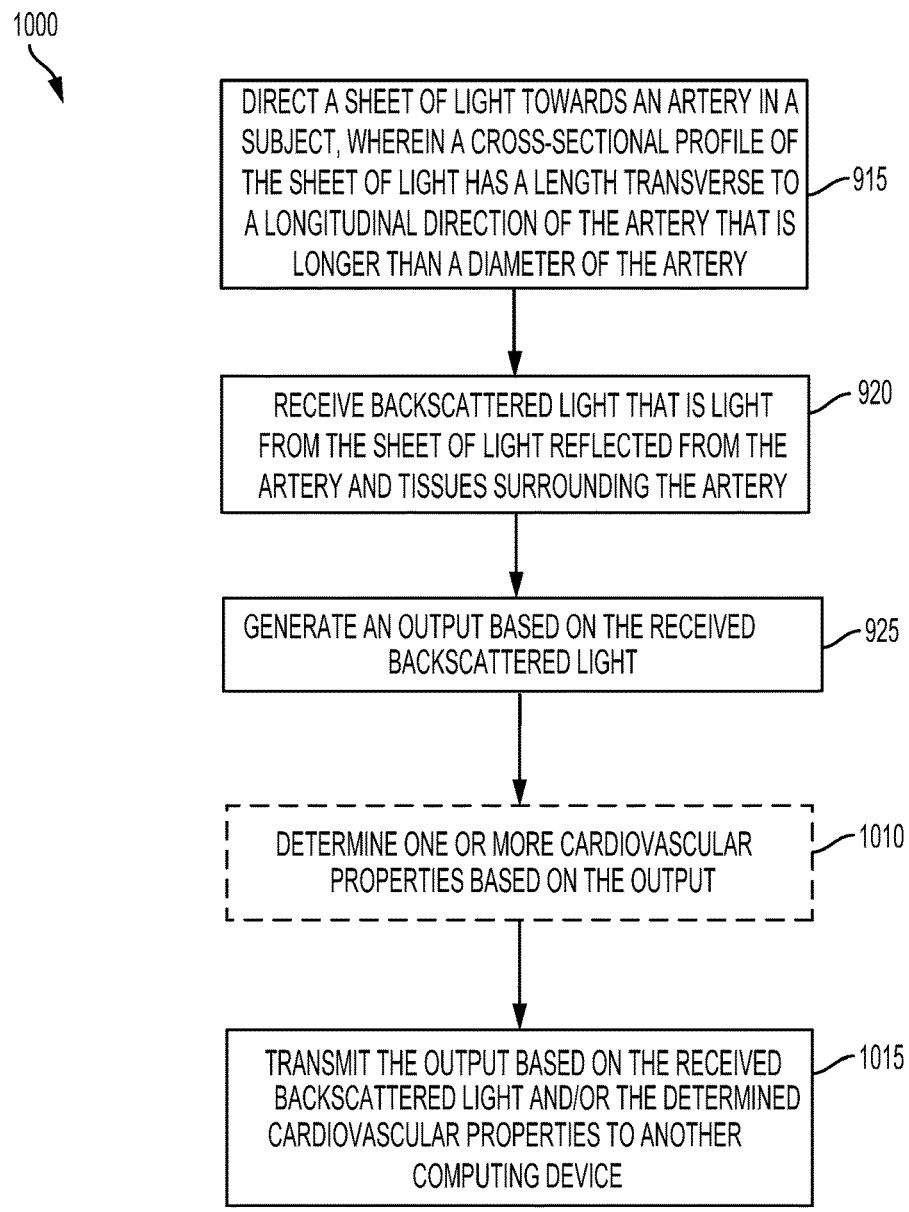
FIG. 10 illustrates another method of measuring cardiovascular properties using an optical sensor according to some embodiments.

FIG. 10 illustrates a method 1000 of using an optical sensor for obtaining measurements of cardiovascular properties in an optical measuring device according to various embodiments. The method 1000 may include operations in blocks 915-925 as described with reference to FIG. 9.

In optional block 1010, the processor (e.g., 320) may receive the output from the one or more light detectors and determine one or more cardiovascular properties based on the output. In some embodiments, the generated output may be in the form of a pulse waveform signal having both alternating current (AC) and direct current (DC) components. The AC signal component may correspond to the optical response of the artery of interest, while the DC signal component may correspond to the optical response of non-dynamic tissues that surround the artery. In order to obtain the AC signal component of the pulse waveform for the artery, the processor may process the pulse waveform signal through a high pass filter having a cut-off frequency in the order of 0.5 Hertz (Hz) or lower.

As part of the operations in optional block 1010, the processor may use the output signal from the one or more light detectors to calculate a variety of cardiovascular properties, such as arterial distension, pulse transit time (PTT), pulse wave velocity (PWV), arterial stiffness, heart rate, heart rate variability, and blood pressure, as well as calibration procedures for one or more of such measurements. For example, in some embodiments, the processor may track changes in the AC signal component over time in order to determine one or more cardiovascular properties, including distension of an artery, for example.

In some embodiments, the processor may determine oxygen levels in the blood (SpO2) from differences in the absorption of two different wavelengths of light. For example, the blood oxygen level may be measured as a ratio between a mean of the measured DC and AC components for two wavelengths of light (e.g., one wavelength may be red (e.g., 660 nanometers (nm)) and the other wavelength may be infrared (e.g., on the order of 950 nm).

In some embodiments, the optical measuring device may include at least two optical sensors spaced apart in parallel to a longitudinal direction of the artery (e.g., illustrated in FIG. 3C) to measure certain cardiovascular properties, such as a pulse transit time (PTT). In such embodiments, in optional block 1010 the processor may compute the pulse wave transit time based on a time shift between the AC signal components of two pulse waveforms detected at the respective optical sensor locations. For example, the processor may determine the time shift by (i) correlating the systolic parts of the two pulse waveforms, (ii) finding the minimum just before the systolic onset of the two pulse waveforms, and then observing the time difference, (iii) finding the maximum and minimum of the two pulse waveforms, identifying a point on the slope corresponding to a given ratio of the wave forms, and determining the time shift between these two points, or (iv) detecting the zero crossing of the high pass filtered versions of the waveforms.

In some embodiments, in optional block 1010 the processor may calculate the heart rate by estimating the time between pulses or by estimating characteristic periodicities in sequence of pulses based on the output received from the one or more light detectors.

In some embodiments, in optional block 1010 the processor may calculate blood pressure based on the signal variation that is synchronous with the heartbeat. For example, blood pressure may be calculated by the processor in optional block 1010 from various combinations of cardiovascular properties determined from the output received from the one or more light detectors. Such cardiovascular properties may include, but are not limited to arterial distension. In some embodiments, details of pulse shapes may also be retrievable from the signal. Such details may reveal information about reflections and may also facilitate estimates of central cardiovascular parameter, which may be aortic pulse wave velocity (PWV) and central blood pressures.

In block 1015, the processor may transmit the one or more cardiovascular properties determined by the processor in optional block 1010 to another computing device, such as via an RF processor (e.g., 330) and an antenna (e.g., 332). For example, the processor may transmit calculated cardiovascular property measurements to a mobile device, such as a smartphone, via a wireless signal, such as Bluetooth or WLAN, for display to an operator. The computing device may store, process, and/or display calculated cardiovascular property measurements. In some embodiments, the output generated by the light detector in block 925 may be transmitted directly to another computing device, such as a smartphone, in block 1015. In such embodiments, the computing device may determine the one or more cardiovascular properties from the output signals, enabling the use of a limited capability processor in the optical sensor.

Those of skill in the art will appreciate that the foregoing method description and the process flow diagram are provided merely as illustrative examples and are not intended to require or imply that the steps of the various embodiments must be performed in the order presented. The operations in the foregoing embodiment methods may be performed in any order. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The steps of a method or algorithm disclosed herein may be embodied in processor-executable software that may stored on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the claims are not intended to be limited to the embodiments shown herein but are to be accorded the widest scope consistent with the claims and the principles and novel features disclosed herein.

What is claimed is:

1. An optical measuring device for measuring cardiovascular properties, comprising:
    a flexible substrate configured as a patch to wrap around a first region and a second region of a subject, the first region movable with respect with the second region;
    a first optical sensor attached to an inner surface of the flexible substrate and comprising a first light source, a first light detector, and a first transmit light guide coupled to the first light source, the first transmit light guide being configured to direct light from the first light source as a first sheet of light towards an artery in the first region, the first light detector being configured to receive first backscattered light and generate a first output based on the received first backscattered light, wherein the first backscattered light is light from the first sheet of light that is reflected from the artery and tissues surrounding the artery in the first region; and
    a second optical sensor attached to the inner surface of the flexible substrate comprising a second light detector, a second light source and a second transmit light guide coupled to the second light source, the second transmit light guide being configured to direct light from the second light source as a second sheet of light towards the artery in the second region, the second light detector being configured to receive second backscattered light and generate a second output based on the received second backscattered light, wherein the second backscattered light is light from the second sheet of light that is reflected from the artery and tissues surrounding the artery in the second region.

2. The optical measuring device of claim 1, wherein a cross-sectional profile of the first sheet of light and of the second sheet of light has a width parallel to a longitudinal direction of the artery that is shorter than, respectively, a length of the first sheet of light and a length of the second sheet of light.

3. The optical measuring device of claim 1, wherein a cross-sectional profile of the first sheet of light and of the second sheet of light has an elliptical, rectangular, triangular, or polygonal shape.

4. The optical measuring device of claim 1, wherein the first transmit light guide includes flexible material and is configured to:
    conform to a partial circumference of a limb of the subject in the first region; and
    direct the first sheet of light towards the first region such that a transverse axis of the first sheet of light extends along and conforms to the partial circumference.

5. The optical measuring device of claim 4, wherein the transverse axis of the first sheet of light extends along the partial circumference of the limb for at least forty degrees.

6. The optical measuring device of claim 1, wherein the first transmit light guide and the second transmit light guide are comprise one or more of optical facets, refractive index structures, a volume hologram, a diffractive surface relief element, or any combination thereof.

7. The optical measuring device of claim 1, wherein the first transmit light guide and the second transmit light guide are comprise a planar optical waveguide, a prism, or any combination thereof.

8. The optical measuring device of claim 1, wherein the first transmit light guide and the second transmit light guide are comprise one or more lenses configured to focus, respectively, the first sheet of light and the second sheet of light at a targeted focal depth.

9. The optical measuring device of claim 8, wherein the one or more lenses of the first transmit light guide and the second transmit light guide are configured to focus, respectively, the first sheet of light and the second sheet of light with a targeted width at the targeted focal depth.

10. The optical measuring device of claim 1, wherein the first transmit light guide and the second transmit light guide are configured to conform to a surface of a limb of the subject.

11. The optical measuring device of claim 1, wherein:
    the first and second light detectors of the first optical sensor and the second optical sensor are configured to receive the first backscattered light and the second backscattered light along a partial circumference of a limb of the subject.

12. The optical measuring device of claim 1, wherein each of the first optical sensor and the second optical sensor comprises a single light detector, the optical measuring device further comprising:
    one or more receive light guides coupled to the single light detector, wherein each of the one or more receive light guides is configured to collect the first backscattered light and the second backscattered light to direct the collected first backscattered light and the collected second backscattered light towards the single light detector of, respectively, the first optical sensor and the second optical sensor.

13. The optical measuring device of claim 1, wherein each of the first optical sensor and the second optical sensor further comprises a plurality of light detectors, the optical measuring device further comprising:
a plurality of receive light guides, wherein each of the plurality of receive light guides is coupled to a respective one of the plurality of light detectors and is configured to collect the backscattered light and direct the collected backscattered light towards the respective one of the plurality of light detectors.

14. The optical measuring device of claim 1, wherein each of the first optical sensor and the second optical sensor comprises one or more light detectors coupled to one or more receive light guides.

15. The optical measuring device of claim 1, wherein the first optical sensor and the second optical sensor comprise a plurality of light detectors distributed along a length of, respectively, the first transmit light guide and the second transmit light guide.

16. The optical measuring device of claim 1, further comprising a processor coupled to the first and second light detectors and configured with processor-executable instructions to determine cardiovascular properties based on the output from the one or more first and second light detectors.

17. The optical measuring device of claim 1, further comprising flexible wired connections attached on the flexible substrate and coupled with each of the first optical sensor and the second optical sensor; wherein the flexible wired connections are configured to accommodate relative movement between the first region and the second region of the subject.

18. The optical measuring device of claim 1, further comprising a processor configured to determine a pulse transit time based on the first output and the second output.

19. The optical measuring device of claim 1, wherein the first light source is configured to emit light of a first wavelength;
wherein the second light source is configured to emit light of a second wavelength;
wherein the optical measuring device further comprises a processor configured to determine a difference between a first degree of absorption of the light of the first wavelength by the artery and a second degree of absorption of the light of the second wavelength by the artery.

20. A method of measuring cardiovascular properties using an optical measuring device applied to a subject, comprising:
directing, using a first light guide attached to an inner surface of a flexible substrate, a first sheet of light from a first light source also attached to the inner surface of the flexible substrate towards an artery in a first region of the subject, the flexible substrate being wrapped around the first region and a second region of the subject, the first region being movable with respect to the second region;
directing, using a second light guide attached to the inner surface of the flexible substrate, a second sheet of light from a second light source also attached to the inner surface of the flexible substrate towards the artery in the second region of the subject;
receiving, using a first light detector attached to the inner surface of the flexible substrate, first backscattered light that is light from the first sheet of light reflected from the artery and tissues surrounding the artery in the first region;
receiving, using a second light detector attached to the inner surface of the flexible substrate, second backscattered light that is light from the second sheet of light reflected from the artery and tissues surrounding the artery in the second region; and
generating an output based on the first backscattered light received by the first light detector and the second backscattered light received by the second light detector.

21. The method of claim 20, further comprising:
determining one or more cardiovascular properties based on the output.

22. The method of claim 20, wherein a cross-sectional profile of the first sheet of light and of the second sheet of light has a width parallel to a longitudinal direction of the artery that is shorter than, respectively, a length of the first sheet of light and a length of the second sheet of light.

23. The method of claim 20, wherein a cross-sectional profile of the first sheet of light and of the second sheet of light has an elliptical, rectangular, triangular, or polygonal shape.

24. The method of claim 20, wherein directing the first sheet of light towards the artery in the subject comprises directing the first sheet of light towards the first region such that a transverse axis of the first sheet of light extends along and conforms to a partial circumference of a limb of the subject.

25. The method of claim 24, wherein:
directing the first sheet of light along the partial circumference of the limb comprises directing the first sheet of light along the partial circumference of the limb for at least forty degrees; and
receiving the first backscattered light comprises receiving the first backscattered light along the partial circumference of the limb.

26. An optical measuring device for measuring cardiovascular properties, comprising:
means for wrapping around a first region and a second region of a subject, the second region being movable with respect to the first region;
means for directing a first sheet of light towards an artery in the first region of the subject;
means for directing a second sheet of light towards the artery in a second region of the subject;
means for receiving first backscattered light that is light from the first sheet of light reflected from the artery and tissues surrounding the artery in the first region;
means for receiving second backscattered light that is light from the second sheet of light reflected from the artery and tissues surrounding the artery in the second region; and
means for generating an output based on the received first backscattered light and the received second backscattered light,
wherein the means for directing the first sheet of light, the means for directing the second sheet of light, the means for receiving the first backscattered light, and the means for receiving the second backscatter light are attached to the means for wrapping around the first region and the second region.

27. The optical measuring device of claim 26, further comprising:
means for determining one or more cardiovascular properties based on the output.

28. The optical measuring device of claim 26, wherein a cross-sectional profile of the first sheet of light and of the second sheet of light has a width parallel to a longitudinal direction of the artery that is shorter than, respectively, a length of the first sheet of light and a length of the second sheet of light.

29. The optical measuring device of claim 26, wherein a cross-sectional profile of the first sheet of light and of the second sheet of light has an elliptical, rectangular, triangular, or polygonal shape.

30. An optical measuring device for measuring cardiovascular properties, comprising:
a flexible substrate configured as a patch to wrap around a first region and a second region of a subject, the first region movable with respect with the second region;
a first optical sensor attached to an inner surface of the flexible substrate and comprising a first light source, a first light detector, and a first transmit light guide coupled to the first light source, the first transmit light guide being configured to direct light from the first light source as a first sheet of light towards an artery in the first region, the first light detector being configured to receive first backscattered light and generate a first output based on the received first backscattered light, wherein the first backscattered light is light from the first sheet of light that is reflected from the artery and tissues surrounding the artery in the first region;
a second optical sensor attached to the inner surface of the flexible substrate comprising a second light detector, a second light source and a second transmit light guide coupled to the second light source, the second transmit light guide being configured to direct light from the second light source as a second sheet of light towards the artery in the second region, the second light detector being configured to receive second backscattered light and generate a second output based on the received second backscattered light, wherein the second backscattered light is light from the second sheet of light that is reflected from the artery and tissues surrounding the artery in the second region; and
a processor coupled to the first optical sensor and the second optical sensor and configured to determine one or more cardiovascular properties based on outputs from the first optical sensor and the second optical sensor.

31. The optical measuring device of claim 30, wherein a cross-sectional profile of the first sheet of light and of the second sheet of light has a width parallel to a longitudinal direction of the artery that is shorter than, respectively, a length of the first sheet of light and a length of the second sheet of light.

32. The optical measuring device of claim 30, wherein a cross-sectional profile of the first sheet of light and of the second sheet of light has an elliptical, rectangular, triangular, or polygonal shape.

* * * * *